(12) United States Patent
Plant et al.

(10) Patent No.: US 8,404,618 B2
(45) Date of Patent: Mar. 26, 2013

(54) HERBICIDAL COMPOSITION

(75) Inventors: Andrew Plant, Bracknell (GB); Willy Thaddaeus Rüegg, Basel (CH); Jean Wenger, Basel (CH); Ulrich Johannes Haas, Basel (DE); Anja Greiner, Basel (CH)

(73) Assignee: Syngenta Limited, Guildford, Surrey (GB)

( * ) Notice: Subject to any disclaimer, the term of this patent is extended or adjusted under 35 U.S.C. 154(b) by 1447 days.

(21) Appl. No.: 11/568,326

(22) PCT Filed: Apr. 29, 2005

(86) PCT No.: PCT/EP2005/004610
§ 371 (c)(1),
(2), (4) Date: Jul. 27, 2007

(87) PCT Pub. No.: WO2005/104848
PCT Pub. Date: Nov. 10, 2005

(65) Prior Publication Data
US 2007/0259786 A1    Nov. 8, 2007

(30) Foreign Application Priority Data

Apr. 30, 2004   (CH) .................................. 0767/04

(51) Int. Cl.
*A01N 25/26* (2006.01)
*A01N 43/00* (2006.01)
*A01N 43/36* (2006.01)

(52) U.S. Cl. .......................... 504/100; 504/138; 504/139

(58) Field of Classification Search .................. None
See application file for complete search history.

(56) References Cited

U.S. PATENT DOCUMENTS 6,555,499 B1 * 4/2003 Glock et al. ................. 504/130
2005/0256004 A1 * 11/2005 Takahashi et al. ........... 504/271

FOREIGN PATENT DOCUMENTS

| EP | 1203768 | 5/2002 |
| EP | 1405853 | 4/2004 |
| WO | 0000031 | 1/2000 |
| WO | 2004014138 | 2/2004 |

OTHER PUBLICATIONS

Sprague C. L. et al: "Enhancing the Margin of Selectivity of RPA 201772 in Zea Mays with Antidotes," Weed Science, Weed Science Society of America, Champaign, IL, US., vol. 47, No. 5, 1999, pp. 492-497, XP000901419, ISSN: 0043-1745, p. 494; table 1.

* cited by examiner

*Primary Examiner* — Alton Pryor
(74) *Attorney, Agent, or Firm* — James Cueva

(57) ABSTRACT

Herbicidal composition comprising a compound of the formula (I) wherein the substituents have the meanings given in claim 1, and a safener.

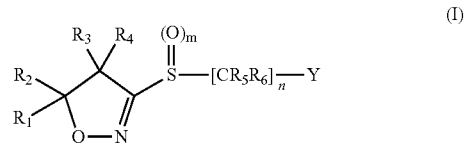

12 Claims, No Drawings

HERBICIDAL COMPOSITION

This application is a 371 of International Application No. PCT/EP2005/004610 filed Apr. 29, 2005, which claims priority to CH 00767/04 filed 30 Apr. 2004, the contents of which are incorporated herein by reference.

The present invention relates to new herbicidal compositions for combating weed grasses and weeds in crops of useful plants, which comprise a herbicide and a safener which preserves the useful plant but not the weed grasses and weeds against the phytotoxic action of the herbicide. The present invention also relates to the use of these compositions for combating weed grasses and weeds in crops of useful plants, in particular in crops of soya, cotton, rape, sugarcane, cereals, e.g. wheat and barley, rice and, in particular, maize.

When herbicides are employed to kill weeds growing among crops, the crops plants may also be damaged. To counteract this problem, various substances have already been proposed as safeners, which are substances capable of protecting the crop plants from the damaging action of the herbicide, while not substantially reducing the effectiveness of the herbicide with a given herbicide. The interaction of herbicides and safeners is complex, and it is difficult to predict which safeners, if any, will be useful with a given herbicide.

It has now been found that the compounds of the formulae S-I to S-X, as defined herein, are suitable for protecting crop plants from the phytotoxic action of a certain class of isoxazoline herbicides which are described e.g. in WO 01/12613, WO 03/000686, WO 2004/014138 and JP (Kokai) 2004-2324. The safeners of the formulae S-I to S-X are known and are described e.g. in U.S. Pat. No. 5,041,157, U.S. Pat. No. 5,541,148, U.S. Pat. No. 5,006,656, EP-A-0 094 349, EP-A-0 551 650, EP-A-0 268 554, EP-A-0 375 061, EP-A-0 174 562, EP-A-492 366, WO 91/7874, WO 94/987, DE-A-19612943, WO 96/29870, WO 98/13361, WO 98/39297, WO 98/27049, EP-A-0 716 073, EP-A-0 613 618, U.S. Pat. No. 5,597,776, EP-A-0430 004, WO 97/45016, WO 99/16744 and WO 03/02205.

According to the invention there is provided a herbicidal composition which is characterized in that it comprises a mixture of a) a herbicidally active amount of a herbicide of the formula I

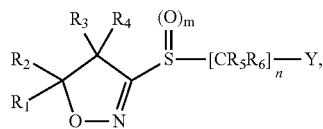

wherein $R_1$ and $R_2$ are each independently of the other hydrogen, $C_1$-$C_{10}$alkyl, $C_3$-$C_8$cycloalkyl or $C_3$-$C_8$cycloalkyl-$C_1$-$C_3$alkyl, or $R_1$ and $R_2$, together with the carbon atom to which $R_1$ and $R_2$ are bonded, form a $C_3$-$C_7$ ring, $R_3$ and $R_4$ are each independently of the other hydrogen, $C_1$-$C_{10}$alkyl, $C_3$-$C_{10}$haloalkyl, $C_3$-$C_8$-cycloalkyl-$C_1$-$C_{10}$alkyl, $C_1$-$C_6$alkoxy-$C_1$-$C_{10}$ alkyl or $C_3$-$C_8$cycloalkyl, or $R_3$ and $R_4$, together with the carbon atom to which $R_3$ and $R_4$ are bonded, form a $C_3$-$C_7$ ring, or $R_1$ with $R_3$ or $R_4$ and together with the carbon atoms to which $R_1$, $R_3$ and $R_4$ are bonded form a $C_5$-$C_8$ ring, or $R_2$ with $R_3$ or $R_4$ and together with the carbon atoms to which $R_2$, $R_3$ and $R_4$ are bonded form a $C_5$-$C_8$ ring;

m is an integer selected from 0, 1 or 2;

$R_5$ and $R_6$ are each independently of the other hydrogen, cyano, $C_1$-$C_{10}$alkyl or $C_1$-$C_{10}$alkoxycarbonyl;

n is an integer selected from 1, 2 or 3;

Y is hydrogen, $C_1$-$C_6$alkoxycarbonyl, carboxyl, $C_2$-$C_6$alkenyl, $C_1$-$C_{10}$alkyl or $C_1$-$C_{10}$alkyl substituted by halogen, $C_1$-$C_6$alkoxy, $C_2$-$C_6$alkenyloxy, $C_2$-$C_6$alkynyloxy, benzyloxy, $C_1$-$C_6$alkoxycarbonyl, carboxyl, hydroxyl or formyl, or Y is phenyl or phenyl substituted by halogen, $C_1$-$C_6$alkyl, $C_1$-$C_6$haloalkyl, $C_1$-$C_6$alkoxy-$C_1$-$C_6$alkyl, hydroxy-$C_1$-$C_6$alkyl, $C_1$-$C_6$alkylthio-$C_1$-$C_6$alkyl, $C_1$-$C_6$alkylsulfinyl-$C_1$-$C_6$alkyl, $C_1$-$C_6$alkylsulfonyl-$C_1$-$C_6$alkyl, $C_1$-$C_6$alkylamino-$C_1$-$C_6$alkyl, di-$C_1$-$C_6$alkylamino-$C_1$-$C_6$alkyl, cyano-$C_1$-$C_6$alkyl or phenoxy-$C_1$-$C_6$alkyl, or Y is phenyl substituted by $C_1$-$C_6$alkoxy or $C_1$-$C_6$alkoxy substituted by halogen, $C_1$-$C_6$alkoxy, $C_2$-$C_6$alkenyl, $C_2$-$C_6$alkynyl, $C_1$-$C_6$alkoxycarbonyl, $C_1$-$C_6$alkylcarbonyl or $C_3$-$C_8$cycloalkyl, or Y is phenyl substituted by $C_2$-$C_6$alkenyl, $C_3$-$C_8$cycloalkoxy, $C_1$-$C_6$alkylthio or $C_1$-$C_6$alkylthiol substituted by halogen or $C_1$-$C_6$alkoxy, or Y is phenyl substituted by $C_1$-$C_6$alkylsulfinyl or $C_1$-$C_6$alkylsulfinyl substituted by halogen or $C_1$-$C_6$alkoxy, or Y is phenyl substituted by $C_1$-$C_6$alkylsulfonyl or $C_1$-$C_6$alkylsulfonyl substituted by halogen or $C_1$-$C_6$alkoxy, or Y is phenyl substituted by benzyloxy, amino or amino substituted by $C_1$-$C_6$alkyl, $C_1$-$C_6$alkylsulfonyl, $C_1$-$C_6$alkylcarbonyl-$C_1$-$C_6$alkyl or $C_1$-$C_6$alkylsulfonyl-$C_1$-$C_6$alkyl, or Y is phenyl substituted by di-$C_1$-$C_6$alkylamino, cyano, nitro, $C_1$-$C_6$alkoxycarbonyl, carboxyl, $C_3$-$C_8$cycloalkoxycarbonyl, $C_2$-$C_6$alkenyloxycarbonyl, $C_2$-$C_6$alkynyloxycarbonyl, benzyloxycarbonyl, phenoxycarbonyl or $C_1$-$C_6$alkylcarbonyloxy or $C_1$-$C_6$alkoxycarbonyl-$C_1$-$C_6$alkyl, or Y is a 5- or 6-membered, mono- or bicyclic aromatic ring which contains one or more nitrogen, oxygen or sulfur atoms as heteroatoms, in which the heteroaromatic ring can be substituted by hydroxyl, mercapto, halogen, $C_1$-$C_{10}$alkyl or $C_1$-$C_{10}$alkyl substituted by hydroxyl, $C_3$-$C_8$cycloalkyl, halo-$C_3$-$C_8$cycloalkyl, $C_1$-$C_4$alkyl-$C_3$-$C_8$cycloalkyl-, $C_1$-$C_{10}$alkoxy, $C_1$-$C_{10}$alkylthio, $C_1$-$C_{10}$alkylsulfonyl, $C_1$-$C_{10}$alkoxycarbonyl, $C_2$-$C_6$haloalkenyl, amino, $C_1$-$C_{10}$alkylamino, $C_1$-$C_6$acylamino, $C_1$-$C_4$haloalkylcarbonylamino, $C_1$-$C_{10}$alkylsulfonylamino, $C_1$-$C_4$haloalkylsulfonylamino, carbamoyl, $C_1$-$C_{10}$alkylcarbamoyl, $C_1$-$C_6$acyl, $C_1$-$C_4$haloalkylcarbonyl, $C_1$-$C_{10}$alkoxyimino, cyano, phenyl or phenoxy, or the heteroaromatic ring can be substituted by $C_1$-$C_4$haloalkyl, $C_3$-$C_8$cycloalkyl, $C_1$-$C_{10}$alkoxy, $C_1$-$C_{10}$alkoxycarbonyl or $C_1$-$C_{10}$alkoxy substituted by $C_1$-$C_{10}$alkoxycarbonyl, phenyl, an aromatic heterocyclic radical, cyano, carbamoyl or $C_1$-$C_{10}$alkylcarbamoyl, or the heteroaromatic ring can be substituted by $C_1$-$C_4$haloalkoxy, $C_3$-$C_8$cycloalkoxy, $C_3$-$C_8$cycloalkyl-$C_1$-$C_3$alkoxy, $C_1$-$C_{10}$alkylthio or $C_1$-$C_{10}$alkylthio substituted by $C_1$-$C_{10}$alkoxycarbonyl, phenyl, an aromatic heterocyclic radical, cyano, carbamoyl or $C_1$-$C_{10}$alkylcarbamoyl, or the heteroaromatic ring can be substituted by $C_1$-$C_4$haloalkylthio, $C_2$-$C_6$alkenyl, $C_2$-$C_6$alkenyloxy, $C_2$-$C_6$alkynyl, $C_2$-$C_6$alkynyloxy, $C_1$-$C_{10}$alkylsulfinyl or $C_1$-$C_{10}$alkylsulfinyl substituted by $C_1$-$C_{10}$alkoxycarbonyl, phenyl, an aromatic heterocyclic radical, cyano, carbamoyl or $C_1$-$C_{10}$alkylcarbamoyl, or the heteroaromatic ring can be substituted by $C_1$-$C_{10}$alkylsulfonyl or $C_1$-$C_{10}$alkylsulfonyl substituted by $C_1$-$C_{10}$alkoxycarbonyl, phenyl, an aromatic heterocyclic radical, cyano, carbamoyl or $C_1$-$C_{10}$alkylcarbamoyl, or the heteroaromatic ring can be substituted by $C_1$-$C_{10}$haloalkylsulfinyl or $C_1$-$C_{10}$alkylsulfonyloxy substituted by $C_1$-$C_{10}$alkoxycarbonyl, phenyl, an aromatic heterocyclic radical, cyano, carbamoyl or $C_1$-$C_{10}$alkylcarbamoyl, or the heteroaromatic ring can be substituted by $C_1$-$C_4$haloalkylsulfonyl, $C_1$-$C_{10}$alkylsulfonyloxy, $C_1$-$C_4$haloalkylsulfonyloxy, phenyl, phenoxy, phenylthio, an aromatic heterocyclic radical, an aromatic heterocyclic radical bonded via an oxygen or sulfur atom or a sulfonyl group, phenylsulfinyl, phenylsulfonyl, phenylsulfonyloxy, $C_1$-$C_6$acyl, $C_1$-$C_4$-haloalkylcarbonyl, benzylcarbonyl, benzoyl, carboxyl, $C_1$-$C_{10}$alkoxycarbonyl, benzyloxycarbonyl, phenoxycarbonyl, cyano, carbamoyl, $C_1$-$C_{10}$alkylcarbamoyl, phenylcarbamoyl, $C_1$-$C_6$acyloxy, $C_1$-$C_4$haloalkylcarbonyloxy, benzylcarbonyloxy, benzoyloxy, nitro, amino, $C_1$-$C_{10}$alkylamino, phenylamino, $C_1$-$C_6$acylamino, $C_1$-$C_6$haloalkylcarbonylamino, benzylcarbonylamino, benzoylamino, $C_1$-$C_{10}$alkylsulfonylamino, $C_1$-$C_6$haloalkylsulfonylamino, benzylsulfonylamino or phenylsulfonylamino;

and b) a herbicide-antagonistically active amount of a safener of the formula S-I

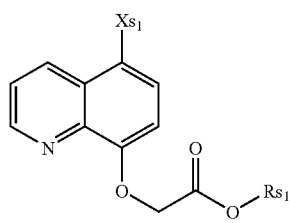

(S-I)

wherein $Xs_1$ is hydrogen or halogen; and $Rs_1$ is hydrogen, $C_3$-$C_8$alkenyl, $C_3$-$C_8$alkynyl, $C_3$-$C_8$cycloalkyl, $C_1$-$C_8$alkyl or $C_1$-$C_8$alkyl substituted by $C_1$-$C_8$alkoxy or $C_3$-$C_8$alkenyloxy, or $Rs_1$ is a cation chosen from the group consisting of the alkali and alkaline earth metals, iron, copper, aluminium, ammonium or quaternary ammonium, sulfonium or phosphonium;

or of a safener of the formula S-II

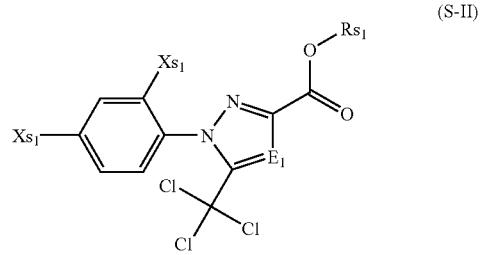

(S-II)

wherein $E_1$ is nitrogen or methine;

$Xs_1$ are each independently of the other hydrogen or halogen; and $Rs_1$ is hydrogen, $C_3$-$C_8$alkenyl, $C_3$-$C_8$alkynyl, $C_3$-$C_8$cycloalkyl, $C_1$-$C_8$alkyl or $C_1$-$C_8$alkyl substituted by $C_1$-$C_8$alkoxy or $C_3$-$C_8$alkenyloxy, or $Rs_1$ is a cation chosen from the group consisting of the alkali and alkaline earth metals, iron, copper, aluminium, ammonium or quaternary ammonium, sulfonium or phosphonium;

or of a safener of the formula S-III

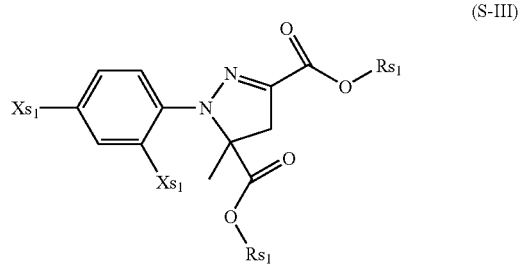

(S-III)

wherein $Xs_1$ are each independently of the other hydrogen or halogen; and $Rs_1$ are each independently of the other hydrogen, $C_3$-$C_8$alkenyl, $C_3$-$C_8$alkynyl, $C_3$-$C_8$cycloalkyl, $C_1$-$C_8$alkyl or $C_1$-$C_8$alkyl substituted by $C_1$-$C_8$alkoxy or $C_3$-$C_8$alkenyloxy, or $Rs_1$ are a cation chosen from the group consisting of the alkali and alkaline earth metals, iron, copper, aluminium, ammonium or quaternary ammonium, sulfonium or phosphonium;

or of a safener of the formula S-IV

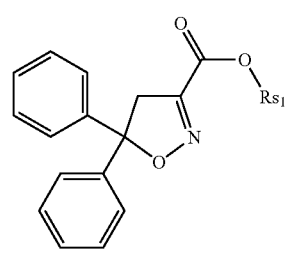

(S-IV)

wherein $Rs_1$ is hydrogen, $C_3$-$C_8$alkenyl, $C_3$-$C_8$alkynyl, $C_3$-$C_8$cycloalkyl, $C_1$-$C_8$alkyl or $C_1$-$C_8$alkyl substituted by $C_1$-$C_8$alkoxy or $C_3$-$C_8$alkenyloxy, or $Rs_1$ is a cation chosen from the group consisting of the alkali and alkaline earth metals, iron, copper, aluminium, ammonium or quaternary ammonium, sulfonium or phosphonium;

or of a safener of the formula S-V

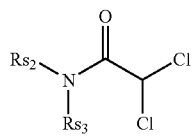
(S-V)

wherein $Rs_2$ and $Rs_3$ are each independently of the other $C_1$-$C_8$alkyl, $C_2$-$C_8$alkenyl or $C_3$-$C_8$cycloalkyl, or
$Rs_2$ and $Rs_3$ together form a radical of the formula

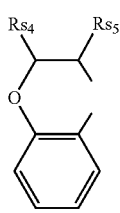

wherein $Rs_4$ and $Rs_5$ are each independently of the other hydrogen or $C_1$-$C_8$alkyl, or
$Rs_2$ and $Rs_3$ together form a radical of the formula

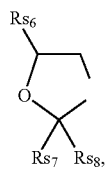

wherein $Rs_7$ and $Rs_8$ are each independently of the other $C_1$-$C_6$alkyl, or
$Rs_7$ and $Rs_8$ together form —(CH$_2$)$_5$—, and
$Rs_6$ is hydrogen, $C_1$-$C_6$alkyl, aryl or heteroaryl;
or of a safener of the formula S-VI

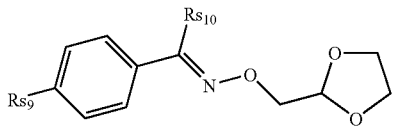
(S-VI)

wherein $Rs_9$ is hydrogen or halogen; and
$Rs_{10}$ is cyano or trifluoromethyl;
or of a safener of the formula S-VII

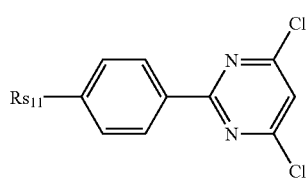
(S-VII)

wherein $Rs_{11}$ is hydrogen or methyl;

or of a safener of the formula S-VIII

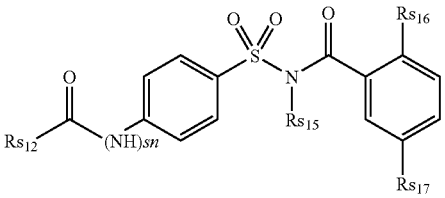
(S-VIII)

wherein sn is 0 or 1;
$Rs_{12}$ is hydrogen, $C_1$-$C_8$alkyl, $C_3$-$C_8$cycloalkyl, $C_3$-$C_8$alkenyl, $C_3$-$C_8$alkynyl or —N(-$Rs_{13}$-$Rs_{14}$);
wherein $Rs_{13}$ and $Rs_{14}$ are each independently of the other hydrogen, $C_1$-$C_8$alkyl, $C_3$-$C_8$cycloalkyl, $C_3$-$C_8$alkenyl or $C_3$-$C_8$alkynyl, or
$Rs_{13}$ and $Rs_{14}$ together form a $C_4$-$C_6$alkylene group, which can be interrupted by oxygen, sulfur, SO, SO$_2$, NH or N($C_1$-$C_4$alkyl);
$Rs_{15}$ is hydrogen or a cation chosen from the group consisting of the alkali and alkaline earth metals, iron, copper, aluminium, ammonium or quaternary ammonium, sulfonium or phosphonium;
$Rs_{16}$ is hydrogen, halogen, $C_1$-$C_8$alkyl or methoxy; and
$Rs_{17}$ is hydrogen, halogen, $C_1$-$C_8$alkyl, trifluoromethyl or $C_1$-$C_8$alkoxy;
or of a safener of the formula S-IX

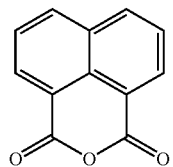
(S-IX)

or of a safener of the formula S-X

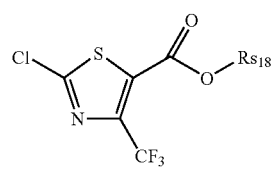
(S-X)

wherein $Rs_{18}$ is benzyl, hydrogen, $C_3$-$C_8$alkenyl, $C_3$-$C_8$alkynyl, $C_3$-$C_8$cycloalkyl, $C_1$-$C_8$alkyl or $C_1$-$C_8$alkyl substituted by $C_1$-$C_8$alkoxy or $C_3$-$C_8$alkenyloxy, or
$Rs_{18}$ is a cation chosen from the group consisting of the alkali and alkaline earth metals, iron, copper, aluminium, ammonium or quaternary ammonium, sulfonium or phosphonium.

In the definition of compound (I) above, alkyl radicals appearing in the substituent definitions are, for example methyl, ethyl, propyl and butyl, and also branched isomers thereof. Haloalkyl radicals include alkyl radicals substituted by one or more halogen, e.g. difluoromethyl or trifluoromethyl, and haloalkoxy radicals include alkoxy radicals substituted by one or more halogen, e.g. difluoromethoxy or 2,2-difluoroethoxy.

Furthermore, according to the invention, there is provided a herbicidal composition which is characterized in that it comprises a mixture of
a) a herbicidally active amount of a herbicide of the formula I

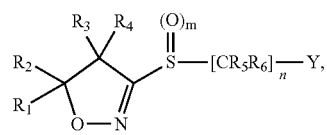

wherein
$R_1$, $R_2$, $R_3$, $R_4$, $R_5$, $R_6$, m and n are defined as above;
Y is hydrogen, $C_1$-$C_6$alkoxycarbonyl, carboxyl, $C_2$-$C_6$alkenyl, $C_1$-$C_{10}$alkyl or $C_1$-$C_{10}$alkyl substituted by halogen, $C_1$-$C_6$alkoxy, $C_2$-$C_6$alkenyloxy, $C_2$-$C_6$alkynyloxy, benzyloxy, $C_1$-$C_6$alkoxycarbonyl, carboxyl, hydroxyl or formyl, or
Y is phenyl or phenyl substituted by halogen, $C_1$-$C_6$alkyl, $C_1$-$C_6$haloalkyl, $C_1$-$C_6$alkoxy-$C_1$-$C_6$alkyl, hydroxy-$C_1$-$C_6$alkyl, $C_1$-$C_6$alkylthio-$C_1$-$C_6$alkyl, $C_1$-$C_6$alkylsulfinyl-$C_1$-$C_6$alkyl, $C_1$-$C_6$alkylsulfonyl-$C_1$-$C_6$alkyl, $C_1$-$C_6$alkylamino-$C_1$-$C_6$alkyl, di-$C_1$-$C_6$alkylamino-$C_1$-$C_6$alkyl, cyano-$C_1$-$C_6$alkyl or phenoxy-$C_1$-$C_6$alkyl, or
Y is phenyl substituted by $C_1$-$C_6$alkoxy or $C_1$-$C_6$alkoxy substituted by halogen, $C_1$-$C_6$alkoxy, $C_2$-$C_6$alkenyl, $C_2$-$C_6$alkynyl, $C_1$-$C_6$alkoxycarbonyl, $C_1$-$C_6$alkylcarbonyl or $C_3$-$C_6$cycloalkyl, or
Y is phenyl substituted by $C_2$-$C_6$alkenyl, $C_3$-$C_8$cycloalkoxy, $C_1$-$C_6$alkylthio or $C_1$-$C_6$alkylthiol substituted by halogen or $C_1$-$C_6$alkoxy, or
Y is phenyl substituted by $C_1$-$C_6$alkylsulfinyl or $C_1$-$C_6$alkylsulfinyl substituted by halogen or $C_1$-$C_6$alkoxy, or
Y is phenyl substituted by $C_1$-$C_6$alkylsulfonyl or $C_1$-$C_6$alkylsulfonyl substituted by halogen or $C_1$-$C_6$alkoxy, or
Y is phenyl substituted by benzyloxy, amino or amino substituted by $C_1$-$C_6$alkyl, $C_1$-$C_6$alkylsulfonyl, $C_1$-$C_6$alkylcarbonyl-$C_1$-$C_6$alkyl or $C_1$-$C_6$alkylsulfonyl-$C_1$-$C_6$alkyl, or
Y is phenyl substituted by di-$C_1$-$C_6$alkylamino, cyano, nitro, $C_1$-$C_6$alkoxycarbonyl, carboxyl, $C_3$-$C_8$cycloalkoxycarbonyl, $C_2$-$C_6$alkenyloxycarbonyl, $C_2$-$C_6$alkynyloxycarbonyl, benzyloxycarbonyl, phenoxycarbonyl or $C_1$-$C_6$alkylcarbonyloxy or $C_1$-$C_6$alkoxycarbonyl-$C_1$-$C_6$alkyl, or
Y is a 5- or 6-membered, mono- or bicyclic aromatic ring which contains one or more nitrogen, oxygen or sulfur atoms as heteroatoms, in which the heteroaromatic ring can be substituted by hydroxyl, mercapto, halogen, $C_1$-$C_{10}$alkyl or $C_1$-$C_{10}$alkyl substituted by hydroxyl, $C_3$-$C_8$cycloalkyl, halo-$C_3$-$C_8$cycloalkyl, $C_1$-$C_4$alkyl-$C_3$-$C_8$cycloalkyl-, $C_1$-$C_{10}$alkoxy, $C_1$-$C_{10}$alkylthio, $C_1$-$C_{10}$alkylsulfonyl, $C_1$-$C_{10}$alkoxycarbonyl, $C_2$-$C_6$haloalkenyl, amino, $C_1$-$C_{10}$alkylamino, $C_1$-$C_6$acylamino, $C_1$-$C_4$haloalkylcarbonylamino, $C_1$-$C_{10}$alkylsulfonylamino, $C_1$-$C_4$haloalkylsulfonylamino, carbamoyl, $C_1$-$C_{10}$alkylcarbamoyl, $C_1$-$C_6$acyl, $C_1$-$C_4$haloalkylcarbonyl, $C_1$-$C_{10}$alkoxyimino, cyano, phenyl or phenoxy, or
the heteroaromatic ring can be substituted by $C_1$-$C_4$haloalkyl, $C_3$-$C_8$cycloalkyl, $C_1$-$C_{10}$alkoxy, $C_1$-$C_{10}$alkoxycarbonyl or $C_1$-$C_{10}$alkoxy substituted by $C_1$-$C_{10}$alkoxycarbonyl, phenyl, an aromatic heterocyclic radical, cyano or carbamoyl, or
the heteroaromatic ring can be substituted by $C_1$-$C_4$haloalkoxy, $C_3$-$C_8$cycloalkoxy, $C_3$-$C_8$cycloalkyl-$C_1$-$C_3$alkoxy, $C_1$-$C_{10}$alkylthio or $C_1$-$C_{10}$alkylthio substituted by $C_1$-$C_{10}$alkoxycarbonyl, phenyl, an aromatic heterocyclic radical, cyano or carbamoyl, or
the heteroaromatic ring can be substituted by $C_1$-$C_4$haloalkylthio, $C_2$-$C_6$alkenyl, $C_2$-$C_6$alkenyloxy, $C_2$-$C_6$alkynyl, $C_2$-$C_6$alkynyloxy, $C_1$-$C_{10}$alkylsulfinyl or $C_1$-$C_{10}$alkylsulfinyl substituted by $C_1$-$C_{10}$alkoxycarbonyl, phenyl, an aromatic heterocyclic radical, cyano or carbamoyl, or
the heteroaromatic ring can be substituted by $C_1$-$C_{10}$alkylsulfonyl or $C_1$-$C_{10}$alkylsulfonyl substituted by $C_1$-$C_{10}$alkoxycarbonyl, phenyl, an aromatic heterocyclic radical, cyano or carbamoyl, or
the heteroaromatic ring can be substituted by $C_1$-$C_{10}$haloalkylsulfinyl or $C_1$-$C_{10}$alkylsulfonyloxy substituted by $C_1$-$C_{10}$alkoxycarbonyl, phenyl, an aromatic heterocyclic radical, cyano or carbamoyl, or
the heteroaromatic ring can be substituted by $C_1$-$C_4$haloalkylsulfonyl, $C_1$-$C_{10}$alkylsulfonyloxy, $C_1$-$C_4$haloalkylsulfonyloxy, phenyl, phenoxy, phenylthio, an aromatic heterocyclic radical, an aromatic heterocyclic radical bonded via an oxygen or sulfur atom or a sulfonyl group, phenylsulfinyl, phenylsulfonyl, phenylsulfonyloxy, $C_1$-$C_4$-haloalkylcarbonyl, benzylcarbonyl, benzoyl, carboxyl, $C_1$-$C_{10}$alkoxycarbonyl, benzyloxycarbonyl, phenoxycarbonyl, cyano, carbamoyl, $C_1$-$C_{10}$alkylcarbamoyl, phenylcarbamoyl, $C_1$-$C_6$acyloxy, $C_1$-$C_4$haloalkylcarbonyloxy, benzylcarbonyloxy, benzoyloxy, nitro, amino, $C_1$-$C_6$alkylamino, phenylamino, $C_1$-$C_6$acylamino, $C_1$-$C_6$haloalkylcarbonylamino, benzylcarbonylamino, benzoylamino, $C_1$-$C_6$alkylsulfonylamino, $C_1$-$C_6$haloalkylsulfonylamino, benzylsulfonylamino or phenylsulfonylamino;
and
b) a herbicide-antagonistically active amount of a safener of the formula S-I to S-X as defined above.

Furthermore, according to the invention, there is provided a herbicidal composition which is characterized in that it comprises a mixture of
a) a herbicidally active amount of a herbicide of the formula Ia

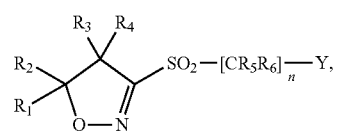

wherein
$R_1$ and $R_2$ are each independently of the other hydrogen, $C_1$-$C_{10}$alkyl, $C_3$-$C_8$cycloalkyl or $C_3$-$C_8$cycloalkyl-$C_1$-$C_3$alkyl, or
$R_1$ and $R_2$, together with the carbon atom to which $R_1$ and $R_2$ are bonded, form a $C_3$-$C_7$ ring,
$R_3$ and $R_4$ are each independently of the other hydrogen, $C_1$-$C_{10}$alkyl, $C_1$-$C_{10}$haloalkyl, $C_3$-$C_8$-cycloalkyl-$C_1$-$C_{10}$alkyl, $C_1$-$C_6$alkoxy-$C_1$-$C_{10}$alkyl or $C_3$-$C_8$cycloalkyl, or
$R_3$ and $R_4$, together with the carbon atom to which $R_3$ and $R_4$ are bonded, form a $C_3$-$C_7$ ring, or R$_1$ with R$_3$ or R$_4$ and together with the carbon atoms to which R$_1$, R$_3$ and R$_4$ are bonded form a C$_5$-C$_8$ ring, or R$_2$ with R$_3$ or R$_4$ and together with the carbon atoms to which R$_2$, R$_3$ and R$_4$ are bonded form a C$_5$-C$_8$ ring;

R$_5$ and R$_6$ are each independently of the other hydrogen, cyano, C$_1$-C$_{10}$alkyl or C$_1$-C$_{10}$alkoxycarbonyl;

n is an integer selected from 1, 2 or 3;

Y is hydrogen, C$_1$-C$_6$alkoxycarbonyl, carboxyl, C$_2$-C$_6$alkenyl, C$_1$-C$_{10}$alkyl or C$_1$-C$_{10}$alkyl substituted by halogen, C$_1$-C$_6$alkoxy, C$_2$-C$_6$alkenyloxy, C$_2$-C$_6$alkynyloxy, benzyloxy, C$_1$-C$_6$alkoxycarbonyl, carboxyl, hydroxyl or formyl, or Y is phenyl or phenyl substituted by halogen, C$_1$-C$_6$alkyl, C$_1$-C$_6$haloalkyl, C$_1$-C$_6$alkoxy-C$_1$-C$_6$alkyl, hydroxy-C$_1$-C$_6$alkyl, C$_1$-C$_6$alkylthio-C$_1$-C$_6$alkyl, C$_1$-C$_6$alkylsulfinyl-C$_1$-C$_6$alkyl, C$_1$-C$_6$alkylsulfonyl-C$_1$-C$_6$alkyl, C$_1$-C$_6$alkylamino-C$_1$-C$_6$alkyl, di-C$_1$-C$_6$alkylamino-C$_1$-C$_6$alkyl, cyano-C$_1$-C$_6$alkyl or phenoxy-C$_1$-C$_6$alkyl, or Y is phenyl substituted by C$_1$-C$_6$alkoxy or C$_1$-C$_6$alkoxy substituted by halogen, C$_1$-C$_6$alkoxy, C$_2$-C$_6$alkenyl, C$_2$-C$_6$alkynyl, C$_1$-C$_6$alkoxycarbonyl, C$_1$-C$_6$alkylcarbonyl or C$_3$-C$_6$cycloalkyl, or Y is phenyl substituted by C$_2$-C$_6$alkenyl, C$_3$-C$_8$cycloalkoxy, C$_1$-C$_6$alkylthio or C$_1$-C$_6$alkylthiol substituted by halogen or C$_1$-C$_6$alkoxy, or Y is phenyl substituted by C$_1$-C$_6$alkylsulfinyl or C$_1$-C$_6$alkylsulfinyl substituted by halogen or C$_1$-C$_6$alkoxy, or Y is phenyl substituted by C$_1$-C$_6$alkylsulfonyl or C$_1$-C$_6$alkylsulfonyl substituted by halogen or C$_1$-C$_6$alkoxy, or Y is phenyl substituted by benzyloxy, amino or amino substituted by C$_1$-C$_6$alkyl, C$_1$-C$_6$alkylsulfonyl, C$_1$-C$_6$alkylcarbonyl-C$_1$-C$_6$alkyl or C$_1$-C$_6$alkylsulfonyl-C$_1$-C$_6$alkyl, or Y is phenyl substituted by di-C$_1$-C$_6$alkylamino, cyano, nitro, C$_1$-C$_6$alkoxycarbonyl, carboxyl, C$_3$-C$_8$cycloalkoxycarbonyl, C$_2$-C$_6$alkenyloxycarbonyl, C$_2$-C$_6$alkynyloxycarbonyl, benzyloxycarbonyl, phenoxycarbonyl or C$_1$-C$_6$alkylcarbonyloxy or C$_1$-C$_6$alkoxycarbonyl-C$_1$-C$_6$alkyl, or Y is a 5- or 6-membered, mono- or bicyclic aromatic ring which contains a nitrogen, oxygen or sulfur atom as a heteroatom, in which the heteroaromatic ring can be substituted by hydroxyl, mercapto, halogen, C$_1$-C$_{10}$alkyl or C$_1$-C$_{10}$alkyl substituted by hydroxyl, C$_3$-C$_8$cycloalkyl, halo-C$_3$-C$_8$cycloalkyl, C$_1$-C$_4$alkyl-C$_3$-C$_8$cycloalkyl-, C$_1$-C$_{10}$alkoxy, C$_1$-C$_{10}$alkylthio, C$_1$-C$_{10}$alkylsulfonyl, C$_1$-C$_{10}$alkoxycarbonyl, C$_2$-C$_6$haloalkenyl, amino, C$_1$-C$_{10}$alkylamino, C$_1$-C$_6$acylamino, C$_1$-C$_4$haloalkylcarbonylamino, C$_1$-C$_{10}$alkylsulfonylamino, C$_1$-C$_4$haloalkylsulfonylamino, carbamoyl, C$_1$-C$_{10}$alkylcarbamoyl, C$_1$-C$_6$acyl, C$_1$-C$_4$haloalkylcarbonyl, C$_1$-C$_{10}$alkoxyimino, cyano, phenyl or phenoxy, or the heteroaromatic ring can be substituted by C$_1$-C$_4$haloalkyl, C$_3$-C$_8$cycloalkoxy, C$_1$-C$_{10}$alkoxy, C$_1$-C$_{10}$alkoxycarbonyl or C$_1$-C$_{10}$alkoxy substituted by C$_1$-C$_{10}$alkoxycarbonyl, phenyl, an aromatic heterocyclic radical, cyano or carbamoyl, or the heteroaromatic ring can be substituted by C$_1$-C$_4$haloalkoxy, C$_3$-C$_8$cycloalkoxy, C$_3$-C$_8$cycloalkyl-C$_1$-C$_3$alkoxy, C$_1$-C$_{10}$alkylthio or C$_1$-C$_{10}$alkylthio substituted by C$_1$-C$_{10}$alkoxycarbonyl, phenyl, an aromatic heterocyclic radical, cyano or carbamoyl, or the heteroaromatic ring can be substituted by C$_1$-C$_4$haloalkylthio, C$_2$-C$_6$alkenyl, C$_2$-C$_6$alkenyloxy, C$_2$-C$_6$alkynyl, C$_2$-C$_6$alkynyloxy, C$_1$-C$_{10}$alkylsulfinyl or C$_1$-C$_{10}$alkylsulfinyl substituted by C$_1$-C$_{10}$alkoxycarbonyl, phenyl, an aromatic heterocyclic radical, cyano or carbamoyl, or the heteroaromatic ring can be substituted by C$_1$-C$_{10}$alkylsulfonyl or C$_1$-C$_{10}$alkylsulfonyl substituted by C$_1$-C$_{10}$alkoxycarbonyl, phenyl, an aromatic heterocyclic radical, cyano or carbamoyl, or the heteroaromatic ring can be substituted by C$_1$-C$_{10}$haloalkylsulfinyl or C$_1$-C$_{10}$alkylsulfonyloxy substituted by C$_1$-C$_{10}$alkoxycarbonyl, phenyl, an aromatic heterocyclic radical, cyano or carbamoyl, or the heteroaromatic ring can be substituted by C$_1$-C$_4$haloalkylsulfonyl, C$_1$-C$_{10}$alkylsulfonyloxy, C$_1$-C$_4$haloalkylsulfonyloxy, phenyl, phenoxy, phenylthio, an aromatic heterocyclic radical, an aromatic heterocyclic radical bonded via an oxygen or sulfur atom or a sulfonyl group, phenylsulfinyl, phenylsulfonyl, phenylsulfonyloxy, C$_1$-C$_4$-haloalkylcarbonyl, benzylcarbonyl, benzoyl, carboxyl, C$_1$-C$_{10}$alkoxycarbonyl, benzyloxycarbonyl, phenoxycarbonyl, cyano, carbamoyl, C$_1$-C$_{10}$alkylcarbamoyl, phenylcarbamoyl, C$_1$-C$_6$acyloxy, C$_1$-C$_4$haloalkylcarbonyloxy, benzylcarbonyloxy, benzoyloxy, nitro, amino, C$_1$-C$_6$alkylamino, phenylamino, C$_1$-C$_6$acylamino, C$_1$-C$_6$haloalkylcarbonylamino, benzylcarbonylamino, benzoylamino, C$_1$-C$_6$alkylsulfonylamino, C$_1$-C$_6$haloalkylsulfonylamino, benzylsulfonylamino or phenylsulfonylamino;

and b) a herbicide-antagonistically active amount of a safener of the formula S-I to S-X as defined above.

Preferred safeners correspond to the formula S-I.1

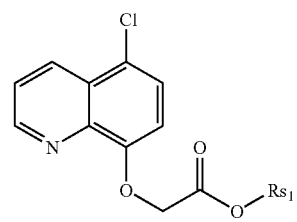

(S-I.1)

wherein Rs$_1$ is hydrogen, C$_3$-C$_8$cycloalkyl, C$_1$-C$_8$alkyl or C$_1$-C$_8$alkyl substituted by C$_1$-C$_8$alkoxy or C$_3$-C$_8$alkenyloxy, or Rs$_1$ is a cation chosen from the group consisting of the alkali and alkaline earth metals, iron, copper, aluminium, ammonium, quaternary ammonium, sulfonium or phosphonium;

or to the formula S-II.1

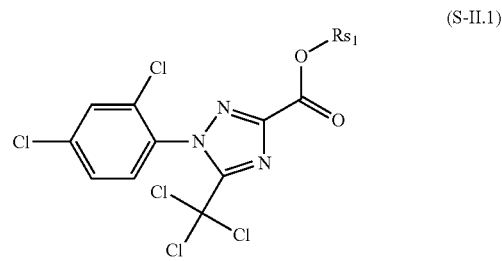

(S-II.1)

wherein $Rs_1$ is $C_1$-$C_8$alkyl or $C_1$-$C_8$alkyl substituted by $C_3$-$C_8$alkenyloxy;
or to the formula S-III.1

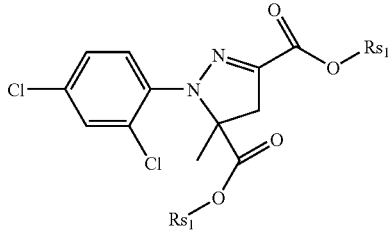
(S-III.1)

wherein $Rs_1$ are each independently of the other $C_1$-$C_8$alkyl or $C_1$-$C_8$alkyl substituted by $C_3$-$C_8$alkenyloxy;
or to the formula S-IV.1

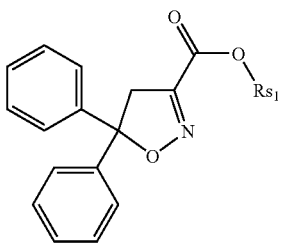
(S-IV.1)

wherein $Rs_1$ is $C_1$-$C_8$alkyl or $C_1$-$C_8$alkyl substituted by $C_3$-$C_8$alkenyloxy;
or to the formula S-IV.1

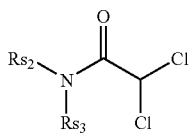
(S-V.1)

wherein $Rs_2$ is $Rs_3$ are each independently of the other $C_2$-$C_8$alkenyl, or
$Rs_2$ and $Rs_3$ together form a radical of the formula

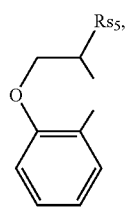

wherein $Rs_5$ is hydrogen or $C_1$-$C_4$alkyl, or
$Rs_2$ and $Rs_3$ together form a radical of the formula

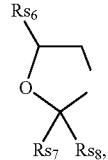

wherein $Rs_7$ and $Rs_8$ are each independently of the other $C_1$-$C_4$alkyl, or
$Rs_7$ and $Rs_8$ together form —$(CH_2)_5$—, and
$Rs_6$ is hydrogen, $C_1$-$C_4$alkyl or

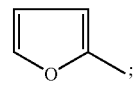

or to the formula S-VI.1

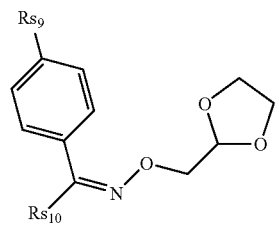
S-VI.1 wherein $Rs_9$ is hydrogen or chlorine; and
$Rs_{10}$ is cyano or trifluoromethyl;
or to the formula S-VII.1

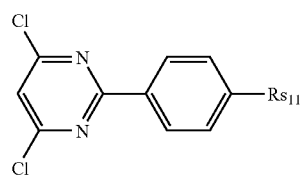
(S-VII.1)

wherein $Rs_{11}$ is hydrogen or methyl;
or to the formula S-VIII.1

(S-VIII.1)

wherein $Rs_{13}$ and $Rs_{14}$ are each independently of the other hydrogen, $C_1$-$C_4$alkyl, $C_3$-$C_6$cycloalkyl, $C_3$-$C_6$alkenyl or $C_3$-$C_6$alkynyl, or
$Rs_{13}$ and $Rs_{14}$ together form a $C_4$-$C_6$alkylene group;

Rs₁₅ is hydrogen or a cation chosen from the group consisting of the alkali and alkaline earth metals, iron, copper, aluminium, ammonium or quaternary ammonium, sulfonium or phosphonium;

$Rs_{16}$ is hydrogen, $C_1$-$C_6$alkyl or methoxy; and $Rs_{17}$ is hydrogen, $C_1$-$C_6$alkyl or $C_1$-$C_6$alkoxy;

or to the formula S-IX.1

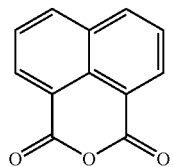

(S-IX.1)

or to the formula S-X.1

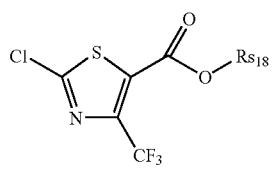

(S-X.1)

wherein $Rs_{18}$ is $C_1$-$C_8$alkyl or $C_1$-$C_8$alkyl substituted by $C_3$-$C_8$alkenyloxy.

Particularly preferred safeners of the formula S-I.1 are cloquintocet-mexyl (CAS RN 99607-70-2) or a lithium, sodium, potassium, calcium, magnesium, aluminium, iron, ammonium, quaternary ammonium, sulfonium or phosphonium salt thereof such as are known from WO 02/34048; of the formula S-II.1 fenchlorazole-ethyl (CAS RN 103112-35-2 and CAS RN 103112-36-3 for the corresponding acid); of the formula S-III.1 mefenpyr-diethyl (CAS RN 135590-91-9 and CAS RN 135591-00-3 for the corresponding di-acid); of the formula S-IV.1 isoxadifen-ethyl (CAS RN 163520-33-0 and CAS RN 209866-92-2 for the corresponding acid); of the formula S-V.1 furilazole (CAS RN 121776-33-8 and CAS RN 121776-57-6 for the corresponding R isomer), benoxacor (CAS RN 98730-04-2), dichlormid (CAS RN 37764-25-3) and MON4660 (CAS RN 71526-07-3); of the formula S-VI.1 oxabetrinil (CAS RN 74782-23-3) and cyometrinil (CAS RN 78370-21-5 and CAS RN 63278-33-1 for the corresponding (Z) isomer); of the formula S-VII.1 fenclorim (CAS RN 3740-92-9); of the formula S-VIII.1 N-cyclopropyl-4-(2-methoxy-benzoylsulfamoyl)-benzamide (CAS RN 221667-31-8) and N-isopropyl-4-(2-methoxy-benzoylsulfamoyl)-benzamide (CAS RN 221668-34-4); of the formula S-IX.1 naphthalic acid anhydride (CAS RN 81-84-5); and of the formula S-X.1 flurazole (CAS RN 72850-64-7).

More particularly preferred safeners of the formula S-I.1 are cloquintocet-mexyl or a lithium, sodium, potassium, calcium, magnesium, aluminium, iron, ammonium, quaternary ammonium, phosphonium or sulfonium salt thereof; of the formula S-II.1 fenchlorazole-ethyl and the corresponding acid; and of the formula S-III.1 mefenpyr-diethyl and the corresponding di-acid; of the formula S-V.1 furilazole and the corresponding R isomer, benoxacor, dichlormid and MON4660.

Yet more particularly preferred safeners of the formula S-I.1 are cloquintocet-mexyl or a lithium, sodium, potassium, calcium, magnesium, aluminium, iron, ammonium, quaternary ammonium, phosphonium or sulfonium salt thereof; of the formula S-II.1 fenchlorazole-ethyl and the corresponding acid; and of the formula S-III.1 mefenpyr-diethyl and the corresponding di-acid; of the formula S-V.1 benoxacor and MON4660.

Even more particularly preferred safeners of the formula S-I.1 are cloquintocet-mexyl; of the formula S-II.1 fenchlorazole-ethyl; of the formula S-III.1 mefenpyr-diethyl; and of the formula S-V.1 benoxacor and MON4660.

Furthermore, particularly preferred safeners of the formula S-I.1 are cloquintocet-mexyl or a lithium, sodium, potassium, calcium, magnesium, aluminium, iron, ammonium, quaternary ammonium, phosphonium or sulfonium salt thereof such as are known from WO 02/34048; of the formula S-II.1 fenchlorazole-ethyl and the corresponding acid; of the formula S-III.1 mefenpyr-diethyl and the corresponding di-acid; of the formula S-IV.1 isoxadifen-ethyl and the corresponding acid; of the formula S-V.1 furilazole and the corresponding R isomer, benoxacor and dichlormid; of the formula S-VI.1 oxabetrinil and cyometrinil and the corresponding (Z) isomer; of the formula S-VII.1 fenclorim; of the formula S-VIII.1 N-cyclopropyl-4-(2-methoxy-benzoylsulfamoyl)-benzamide and N-isopropyl-4-(2-methoxy-benzoylsulfamoyl)-benzamide; of the formula S-IX.1 naphthalic acid anhydride; and of the formula S-X.1 flurazole.

Furthermore, particularly preferred safeners of the formula S-I.1 are cloquintocet-mexyl or sulfonium or phosphonium salts thereof such as are known from WO 02/34048; of the formula S-II.1 fenchlorazole-ethyl and the corresponding acid); of the formula S-III.1 mefenpyr-diethyl and the corresponding di-acid; of the formula S-IV.1 isoxadifen-ethyl and the corresponding acid; of the formula S-V.1 furilazole and the corresponding R isomer, benoxacor and dichlormid; of the formula S-VI.1 oxabetrinil and cyometrinil and the corresponding (Z) isomer; of the formula S-VII.1 fenclorim; of the formula S-VIII.1 N-cyclopropyl-4-(2-methoxy-benzoylsulfamoyl)-benzamide and N-isopropyl-4-(2-methoxy-benzoylsulfamoyl)-benzamide; of the formula S-IX.1 naphthalic acid anhydride; and of the formula S-X.1 flurazole.

Preferred compounds of the formula I are those wherein $R_1$ and $R_2$ are each independently of the other $C_1$-$C_{10}$alkyl or $C_3$-$C_8$cycloalkyl, or $R_1$ and $R_2$, together with the carbon atom to which $R_1$ and $R_2$ are bonded, form a $C_3$-$C_7$ ring, more preferably $R_1$ and $R_2$ are both methyl.

Further preferred compounds of the formula I are those wherein $R_3$ and $R_4$ are each independently of the other hydrogen, $C_1$-$C_{10}$alkyl or $C_3$-$C_8$cycloalkyl, or $R_3$ and $R_4$, together with the carbon atom to which $R_3$ and $R_4$ are bonded, form a $C_3$-$C_7$ ring, more preferably $R_3$ and $R_4$ are both hydrogen.

In another group of preferred compounds, m is 1 or 2, more preferably m is 2.

In a further group of preferred compounds of the formula I, $R_5$ and $R_6$ are each independently of the other hydrogen, methyl, methoxycarbonyl or ethoxycarbonyl, more preferably $R_5$ and $R_6$ are both hydrogen.

In another group of preferred compounds, n is 1.

In a further group of preferred compounds of the formula I, Y is phenyl or phenyl substituted by $C_1$-$C_6$alkyl, $C_1$-$C_6$haloalkyl, $C_1$-$C_6$alkoxy-$C_1$-$C_6$alkyl, $C_1$-$C_6$alkoxy, $C_1$-$C_6$haloalkoxy, $C_1$-$C_6$alkoxy-$C_1$-$C_6$alkoxy or halogen.

In a further group of preferred compounds of the formula I, Y is a 5- or 6-membered mono- or bicyclic aromatic ring which contains one or more nitrogen, oxygen or sulfur atoms as heteroatoms, in which the heteroaromatic ring can be substituted by $C_1$-$C_{10}$alkyl or $C_1$-$C_{10}$alkyl substituted by $C_1$-$C_{10}$alkoxy, or the heteroaromatic ring can be substituted by $C_1$-$C_{10}$alkylsulfonyl, $C_1$-$C_4$haloalkyl, $C_3$-$C_8$cycloalkyl, $C_1$-$C_{10}$alkoxy, $C_1$-$C_4$haloalkoxy, $C_1$-$C_{10}$alkoxycarbonyl, $C_3$-$C_8$cycloalkyl-$C_1$-$C_3$alkoxy, $C_1$-$C_{10}$alkylthio, phenyl, phenoxy, $C_1$-$C_4$haloalkylcarbonyl, cyano, nitro, halogen, carbamoyl, $C_1$-$C_{10}$alkylcarbamoyl or phenylcarbamoyl.

Furthermore, in a further group of preferred compounds of the formula I, Y is a 5- or 6-membered mono- or bicyclic aromatic ring which contains a nitrogen, oxygen or sulfur atom as a heteroatom, in which the heteroaromatic ring can be substituted by $C_1$-$C_{10}$alkyl or $C_1$-$C_{10}$alkyl substituted by $C_1$-$C_{10}$alkoxy; or the heteroaromatic ring can be substituted by $C_1$-$C_{10}$alkylsulfonyl, $C_1$-$C_4$haloalkyl, $C_3$-$C_8$cycloalkyl, $C_1$-$C_{10}$alkoxy, $C_1$-$C_{10}$haloalkoxy, $C_1$-$C_{10}$alkoxycarbonyl, $C_3$-$C_8$cycloalkyl-$C_1$-$C_3$alkoxy, $C_1$-$C_{10}$alkylthio, phenyl, phenoxy, $C_1$-$C_4$haloalkylcarbonyl, cyano, nitro, halogen, carbamoyl, $C_1$-$C_{10}$alkylcarbamoyl or phenylcarbamoyl.

In a further group of preferred compounds of the formula I, Y is thienyl, pyrazolyl, isoxazolyl, isothiazolyl, pyridyl or pyrimidyl.

In a further group of preferred compounds of the formula I, Y is thien-3-yl, pyrazol-4-yl, pyrazol-5-yl, isoxazol-4-yl, isothiazol-4-yl, pyridin-3-yl or pyrimidin-5-yl.

A most preferred compound of the formula I is 3-(5-difluoromethoxy-1-methyl-3-trifluoromethyl-1H-pyrazol-4-yl-methylsulfonyl)-5,5-dimethyl-4,5-dihydroisoxazole, which is compound of the formula 1.27 in Table 1 below.

Particularly suitable compounds of the formula I are summarized in the following table.

TABLE 1

Examples of compounds of the formula I

| | |
|---|---|
| 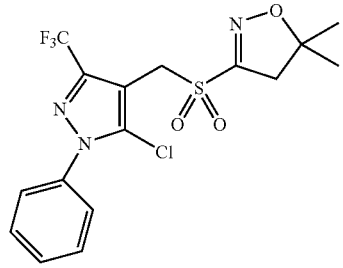 [SMILES: CC1(C)CC(S(=O)(=O)Cc2c(C(F)(F)F)nn(-c3ccccc3)c2Cl)=NO1] | 1.1 |
| 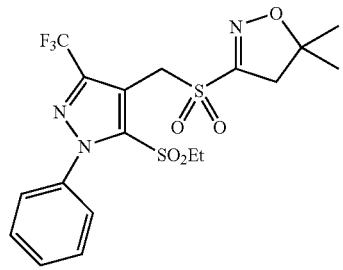 | 1.2 |
| 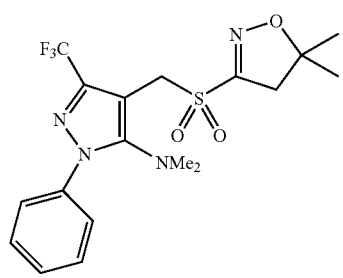 [SMILES: CN(C)c1c(CS(=O)(=O)C2=NOC(C)(C)C2)c(C(F)(F)F)nn1-c1ccccc1] | 1.3 |
| 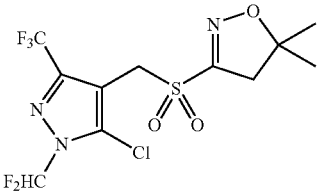 [SMILES: CC1(C)CC(S(=O)(=O)Cc2c(C(F)(F)F)nn(C(F)F)c2Cl)=NO1] | 1.4 |
| 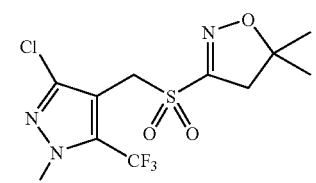 | 1.5 |
| 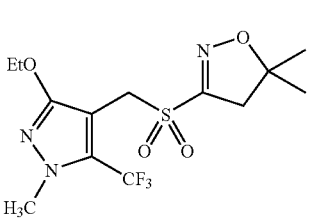 [SMILES: CCOc1nn(C)c(C(F)(F)F)c1CS(=O)(=O)C1=NOC(C)(C)C1] | 1.6 |
| 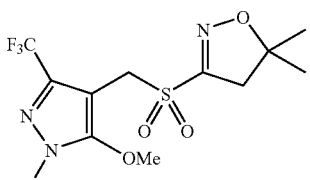 | 1.7 |
| 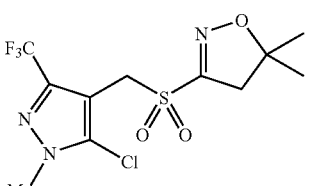 | 1.8 |
| 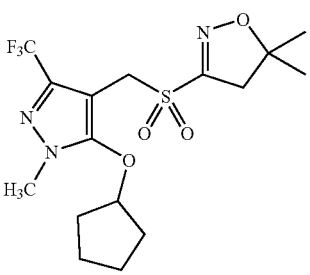 [SMILES: Cn1nc(C(F)(F)F)c(CS(=O)(=O)C2=NOC(C)(C)C2)c1OC1CCCC1] | 1.9 |
| 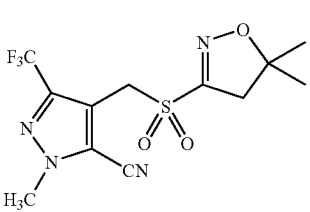 [SMILES: Cn1nc(C(F)(F)F)c(CS(=O)(=O)C2=NOC(C)(C)C2)c1C#N] | 1.10 |

TABLE 1-continued

Examples of compounds of the formula I

| Structure | No. |
|---|---|
| (3-Cl, 5-Cl, 1-Et pyrazole-4-CH2-SO2-dimethylisoxazoline) | 1.11 |
| (3-CF2H, 5-Cl, 1-Me pyrazole-4-CH2-SO2-dimethylisoxazoline) | 1.12 |
| (3-Cl, 5-F, 1-Me pyrazole-4-CH2-SO2-dimethylisoxazoline) | 1.13 |
| (3-CF3, 5-Cl, 1-Me pyrazole-4-CH2-SO2-dimethylisoxazoline) | 1.14 |
| (3-Cl, 5-CF3, 1-Me pyrazole-4-CH2-SO2-dimethylisoxazoline) | 1.15 |
| (3-Cl, 5-F, 1-Me pyrazole-4-CH2-SO2-dimethylisoxazoline) | 1.16 |
| (4,6-dichloropyrimidine-5-CH2-SO2-dimethylisoxazoline) | 1.17 |
| (3-CF3, 5-OiPr, 1-Me pyrazole-4-CH2-SO2-dimethylisoxazoline) | 1.18 |
| (3-CF3, 5-OnPr, 1-Me pyrazole-4-CH2-SO2-dimethylisoxazoline) | 1.19 |
| (3-CF3, 5-OtBu, 1-Me pyrazole-4-CH2-SO2-dimethylisoxazoline) | 1.20 |
| (3-CF3, 5-OnBu, 1-Me pyrazole-4-CH2-SO2-dimethylisoxazoline) | 1.21 |
| (3-CF3, 5-O-cyclohexyl, 1-Me pyrazole-4-CH2-SO2-dimethylisoxazoline) | 1.22 |
| (3-CF3, 5-O-CH2-cyclopropyl, 1-Me pyrazole-4-CH2-SO2-dimethylisoxazoline) | 1.23 |
| (3-CF3, 5-O-CH2-cyclopentyl, 1-Me pyrazole-4-CH2-SO2-dimethylisoxazoline) | 1.24 |

TABLE 1-continued

Examples of compounds of the formula I

TABLE 1-continued
Examples of compounds of the formula I
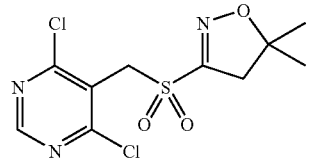 [SMILES: CC1(C)CC(S(=O)(=O)Cc2c(Cl)ncnc2Cl)=NO1] 1.40
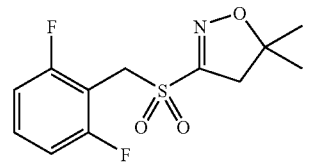 [SMILES: CC1(C)CC(S(=O)(=O)Cc2c(F)cccc2F)=NO1] 1.41
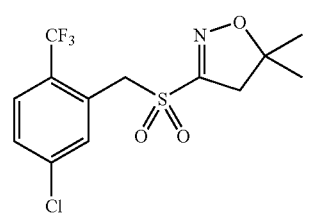 1.42
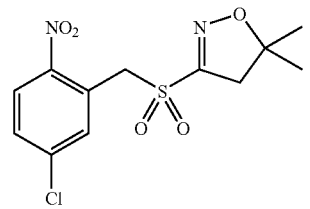 [SMILES: CC1(C)CC(S(=O)(=O)Cc2cc(Cl)ccc2[N+](=O)[O-])=NO1] 1.43
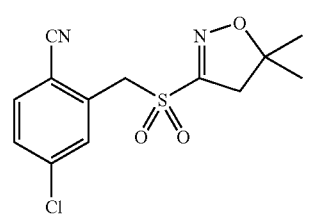 [SMILES: CC1(C)CC(S(=O)(=O)Cc2cc(Cl)ccc2C#N)=NO1] 1.44
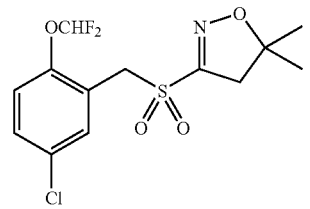 [SMILES: CC1(C)CC(S(=O)(=O)Cc2cc(Cl)ccc2OC(F)F)=NO1] 1.45
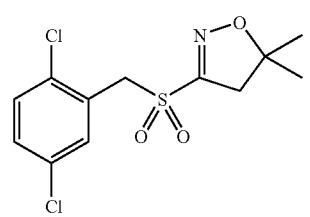 [SMILES: CC1(C)CC(S(=O)(=O)Cc2cc(Cl)ccc2Cl)=NO1] 1.46
TABLE 1-continued
Examples of compounds of the formula I
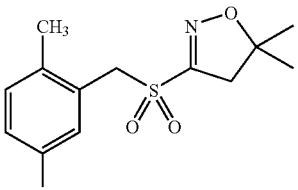 1.47
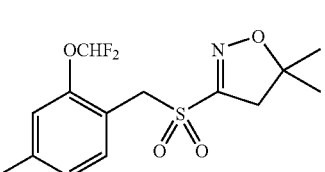 1.48
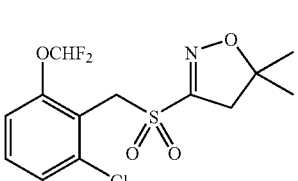 1.49
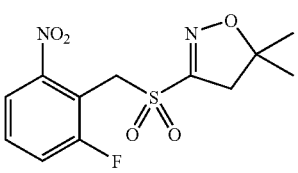 [SMILES: CC1(C)CC(S(=O)(=O)Cc2c(F)cccc2[N+](=O)[O-])=NO1] 1.50
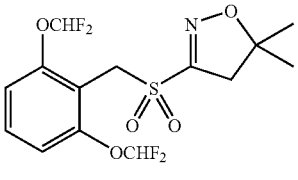 [SMILES: CC1(C)CC(S(=O)(=O)Cc2c(OC(F)F)cccc2OC(F)F)=NO1] 1.51
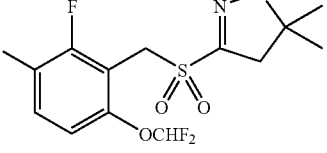 1.52
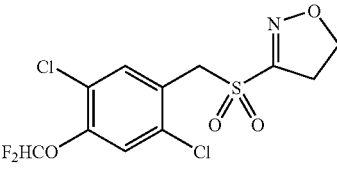 1.53
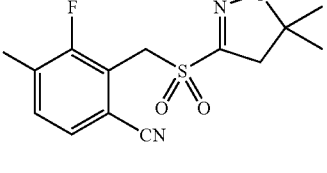 1.54

TABLE 1-continued

Examples of compounds of the formula I 1.55

[Structure: pyrazole with F3C, N-N, H3C on N, CH2-SO2-isoxazoline with gem-dimethyl, OCF3 substituent]

1.56

[Structure: pyrazole with F3C, N-N, Et on N, CH2-SO2-isoxazoline with gem-dimethyl, OCF3 substituent]

1.57

[Structure: pyrazole with F3C, N-N, H3C on N, CH2-S(O)-isoxazoline with gem-dimethyl, OCHF2 substituent]

It has been found that, in particular, good results can be achieved with combinations of the above mentioned compounds of the formulae 1.1 to 1.57 with the safeners cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride and flurazole.

The combinations of compound of the formula 1.27 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can be used with particular advantage. A particularly preferred combination is the combination of compound of the formula 1.27 with benoxacor, in particular when used to safen compound of the formula 1.27 on maize, more particularly in post-emergent use. Further particularly preferred combinations are the combinations of compound of the formula 1.27 with cloquintocet-mexyl, compound of the formula 1.27 with MON4660, compound of the formula 1.27 with mefenpyr-diethyl, and compound of the formula 1.27 with fenchlorazole-ethyl, in particular when used to safen compound of the formula 1.27 on wheat or barley, more particularly in pre-emergent use.

The combinations of compound of the formula 1.28 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage.

The combinations of compound of the formula 1.29 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage.

The combinations of compound of the formula 1.34 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage.

The combinations of compound of the formula 1.41 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage. Particularly preferred combinations are the combinations of a compound of the formula 1.41 with benoxacor, compound of the formula 1.41 with dichlormid, compound of the formula 1.41 with furilazole, and compound of the formula 1.41 with N-isopropyl-4-(2-methoxy-benzoylsulfamoyl)-benzamide, in particular when used to safen compound of formula 1.41 on maize, more particularly in pre-emergent use.

The combinations of compound of the formula 1.43 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage.

The combinations of compound of the formula 1.55 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage.

The combinations of compound of the formula 1.56 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage.

The combinations of compound of the formula 1.57 with cloquintocet-mexyl, fenchlorazole-ethyl, mefenpyr-diethyl, isoxadifen-ethyl, furilazole and the R isomer thereof, benoxacor, dichlormid, MON4660, oxabetrinil, cyometrinil and the (Z) isomer thereof, fenclorim, N-cyclopropyl-4-(2-methoxybenzoylsulfamoyl)-benzamide, N-isopropyl-4-(2-methoxybenzoylsulfamoyl)-benzamide, naphthalic acid anhydride or flurazole can likewise be used with particular advantage. Particularly preferred combinations are the combinations of compound of the formula 1.57 with cloquintocet-mexyl, compound of the formula 1.57 with MON4660, compound of the formula 1.57 with mefenpyr-diethyl, and compound of the formula 1.57 with fenchlorazole-ethyl, in particular when used to safen compound of the formula 1.57 on wheat or barley, more particularly in pre-emergent use.

Furthermore, it has been found that, in particular, good results can be achieved with combinations of the above mentioned compounds of the formulae 1.1 to 1.56 with the safeners cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoylsulfamoyl)-benzamide, N-isopropyl-4-(2-methoxy-benzoylsulfamoyl)-benzamide, naphthalic acid anhydride and flurazole.

The combinations of compound of the formula 1.27 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can be used with particular advantage.

The combinations of compound of the formula 1.28 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The combinations of compound of the formula 1.29 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The combinations of compound of the formula 1.34 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The combinations of compound of the formula 1.41 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The combinations of compound of the formula 1.43 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The combinations of compound of the formula 1.55 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The combinations of compound of the formula 1.56 with cloquintocet-mexyl, fenchlorazole-ethyl, mefenpyr-diethyl, isoxadifen-ethyl, furilazole and the R isomer thereof, benoxacor, dichlormid, oxabetrinil, cyometrinil and the (Z) isomer thereof, fenclorim, N-cyclopropyl-4-(2-methoxy-benzoyl-sulfamoyl)-benzamide, N-isopropyl-4-(2-methoxy-benzoyl-sulfamoyl)-benzamide, naphthalic acid anhydride or flurazole can likewise be used with particular advantage.

The invention also relates to a method of combating weed grasses and weeds in crops of useful plants, which comprises treating the useful plants, seed or cuttings thereof or the growing area thereof simultaneously or at separate times with a herbicidally active amount of the herbicide of the formula I and a herbicide-antagonistically active amount of a safener of the formula S-I to S-X.

Possible crop plants which can be protected by the safeners of the formula S-I to S-X from the harmful action of the above mentioned herbicides are, in particular, soya, cotton, rape, sugarcane, cereals, e.g. wheat and barley, rice and, specifically, maize.

Furthermore, possible crop plants which can be protected by the safeners of the formula S-I to S-X from the harmful action of the above mentioned herbicides are, in particular, soya, cotton, rape and, specifically, maize.

Crops are also to be understood as meaning those which have been made tolerant towards herbicides or herbicide classes (e.g. ALS, GS, EPSPS, PPO and HPPD inhibitors) by conventional breeding or genetic engineering methods. An example of crops which have been made tolerant e.g. towards imidazolinones, such as imazamox, by conventional breeding methods is Clearfield® summer rape (Canola). Examples of crops which have been made tolerant towards herbicides by genetic engineering methods are e.g. glyphosate- or glufosinate-resistant maize varieties, which are commercially obtainable under the trade name RoundupReady® or LibertyLink®. The weeds to be combated can be either monocotyledonous or dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are furthermore to be understood as meaning those which, by genetic engineering methods, have been made resistant to harmful insects, such as, for example, Bt maize (resistant to the corn borer), Bt cotton (resistant to the cotton-boll weevil) and also Bt potatoes (resistant to the potato beetle). Examples of Bt maize are the Bt-176 maize hybrids of NK® (Syngenta Seeds). The Bt toxin is a protein which is formed naturally by *Bacillus thuringiensis* soil bacteria. Examples of toxins and transgenic plants which can synthesize such toxins are described in EP-A-451 878, EP-A-374 753, WO 93/07278, WO 95/34656, WO 03/052073 and EP-A-427 529. Examples of transgenic plants which contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and seed thereof can be resistant both to herbicides and at the same time to insect feeding (stacked transgenic events). Seed can have, for example, the ability to express an insecticidally active Cry3 protein and at the same can be tolerant towards glyphosate. Crops are also to be understood as meaning those which are obtained by conventional breeding or genetic engineering methods and contain so-called output traits (e.g. improved storage stability, higher nutritional value and improved taste).

Growing areas are understood as meaning the areas of soil on which the crop plants are already growing or which are already charged with seed of these crop plants, and also soils intended for cultivation with these crop plants.

The compounds of formula I according to the invention can also be used in combination with other herbicides. In particular, the following mixtures of the compound of formula I are important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfaron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl) phenoxy]-2-pyridyloxy]acetic acid ethyl ester.

The mixing partners of the compound of formula I may also be in the form of esters or salts, as mentioned e.g. in The Pesticide Manual, 12th Edition (BCPC), 2000.

The mixing ratio of the compound of formula I to the mixing partner is preferably from 1:100 to 1000:1.

The mixtures can advantageously be used in the above-mentioned formulations (in which case "active ingredient" relates to the respective mixture of compound of formula I with the mixing partner).

The compositions according to the invention are suitable for all the conventional methods of application in agriculture, such as e.g. pre-emergent application, post-emergent application and seed dressing. Depending on the intended use, a safener of the formula S-I to S-X can be employed for pretreatment of the seed of the crop plant (dressing of the seed or cuttings) or can be introduced into the soil before or after sowing. However, it can also be applied by itself or together with the herbicide before or after emergence of the plants. The treatment of the plants or seed with the safener can therefore in principle be carried out independently of the time of application of the herbicide. Treatment of the plants by simultaneous application of herbicide and safener (e.g. as a tank mix) is as a rule preferred. The application rate of safener to herbicide to be applied largely depends on the method of use. For field treatment, as a rule 0.001 to 5.0 kg of safener/ha, preferably 0.001 to 0.5 kg of safener/ha, and as a rule between 0.001 to 2 kg of herbicide/ha, but preferably between 0.005 to 1 kg/ha are applied. For seed dressing, in general 0.001 to 10 g of safener/kg of seed, preferably 0.05 to 2 g of safener/kg of seed are applied. If the safener is applied in liquid form, with soaking of the seed, shortly before sowing, safener solutions which contain the active compound in a concentration of 1 to 10,000, preferably 100 to 1,000 ppm are expediently used.

A mixture of a herbicidally active amount of the compound of the formula I and a herbicide-antagonistic amount of the compound of the formula S-I to S-X can be employed in unchanged form as a herbicidal composition. However, as a rule the compositions according to the invention are formulated in various ways using formulation auxiliaries, such as carrier substances, solvents and surface-active substances. The formulations can be in various physical forms, e.g. as dusting powders, gels, wettable powders, water-dispersible granules, water-dispersible tablets, effervescent pressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-concentrates (with water or a water-miscible organic solvent as the carrier), impregnated polymer films or in other forms known e.g. from the Manual on Development and Use of FAO Specifications for Plant Protection Products, 5th Edition, 1999. These formulations either can be used directly, or they are diluted before use. The dilutions can be prepared, for example, with water, liquid fertilizers, micronutrients, biological organisms, oil or solvents.

The formulations can be prepared e.g. by mixing the active compound with formulation auxiliaries in order to obtain compositions in the form of finely divided solids, granules, solutions, dispersions or emulsions. The active compounds can also be formulated with other auxiliaries, such as, for example, finely divided solids, mineral oils, oils of plant or animal origin, modified oils of plant or animal origin, organic solvents, water, surface-active substances or combinations thereof. The active compounds can also be contained in very fine microcapsules made of a polymer. Microcapsules contain the active compounds in a porous carrier. This allows release of the active compounds into the environment in controlled amounts (e.g. slow release). Microcapsules conventionally have a diameter of 0.1 to 500 micron. They contain active compounds in an amount of approx. 25 to 95 wt. % of the capsule weight. The active compounds can be in the form of a monolithic solid, fine particles distributed in a solid or liquid, or a suitable solution. The enclosing membranes comprise, for example, natural and synthetic gums, cellulose, styrene/butadiene copolymers, polyacrylonitrile, polyacrylate, polyester, polyamides, polyureas, polyurethane or chemically modified polymers and starch xanthates or other polymers which are known to the expert in this connection. Alternatively, very fine microcapsules in which the active compound is contained in the form of finely divided particles in a solid matrix of base substance, but the microcapsules are not surrounded by a shell, can be formed.

The formulation auxiliaries which are suitable for the preparation of the compositions according to the invention are known per se. Liquid carriers which can be used are: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethylsulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethylene glycol, ethyl lactate, ethylene glycol butyl ether, ethylene glycol methyl ether, gamma-butyrolactone, glycerol, glycerol acetate, glycerol diacetate, glycerol triacetates, hexadecane, hexylene glycol, isoamyl acetate, isobornyl acetates, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is in general the carrier of choice for dilution of the concentrates. Suitable solid carriers are e.g. talc, titanium dioxide, pyrophyllite alumina, silica, attapulgite alumina, kieselguhr, limestone, calcium carbonate, bentonite, calcium montmorillonite, cotton-seed husks, wheat flour, soya flour, pumice, wood flour, ground walnut shells, lignin and similar substances such as are described, for example, in CFR 180.1001. (c) & (d).

A large number of surface-active substances can advantageously be used both in solid and in liquid formulations, in particular in those which can be diluted with a carrier before use. Surface-active substances can be anionic, cationic, nonionic or polymeric, and they can be employed as emulsifying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)-sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and dialkyl phosphate esters; as well as further substances described e.g. in McCutcheon's Detergents and Emulsifiers Annual, MC Publishing Corp., Ridgewood N.J., 1981.

Further auxiliaries which can conventionally be used in pesticidal formulations include crystallization inhibitors, viscosity-modifying substances, suspending agents, dyestuffs, antioxidants, foams, light absorption agents, mixing auxiliaries, defoamers, complexing agents, neutralizing or pH-modifying substances and buffers, corrosion inhibitors, fragrances, wetting agents, uptake enhancers, micronutrients, softeners, slip agents, lubricants, dispersing agents, thickeners, antifreezes, microbiocidal agents, and furthermore liquid and solid fertilizers.

The formulations can also comprise additional active substances, e.g. further herbicides, plant growth regulators, fungicides or insecticides.

The compositions according to the invention can furthermore comprise an additive comprising an oil of plant or animal origin, a mineral oil, alkyl esters of these oils or mixtures of these oils and oil derivatives. The application rates of oil additive in the composition according to the invention is as a rule between 0.01 and 10%, based on the spray liquor. For example, the oil additive can be added into the spray tank in the desired concentration after preparation of the spray liquor. Preferred oil additives comprise mineral oils or an oil of plant origin, such as, for example, rape oil, olive oil or sunflower oil, emulsified vegetable oil, such as AMIGO® (Rhône-Poulenc Canada Inc.), alkyl esters of oils of plant origin, such as, for example, the methyl derivatives, or an oil of animal origin, such as fish oil or beef tallow. A preferred additive substantially comprises e.g. as active components 80 wt. % of alkyl esters of fish oils and 15 wt. % of methylated rape oil, as well as 5 wt. % of conventional emulsifiers and pH modifiers. Particularly preferred oil additives comprise alkyl esters of $C_8$-$C_{22}$ fatty acids, the methyl derivatives of $C_{12}$-$C_{18}$ fatty acids, for example the methyl esters of lauric acid, palmitic acid and oleic acid, being of importance in particular. These esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). These and other oil derivatives are also known from the Compendium of Herbicide Adjuvants, 5th Edition, Southern Illinois University, 2000.

The application and the action of the oil additives can be improved still further by combination with surface-active substances, such as nonionic, anionic or cationic surfactants. Examples of suitable anionic, nonionic and cationic surfactants are listed in WO 97/34485 on pages 7 and 8. Preferred surface-active substances are anionic surfactants of the dodecylbenzenesulfonate type, in particular the calcium salts thereof, and nonionic surfactants of the fatty alcohol ethoxylate type. Ethoxylated $C_{12}$-$C_{22}$-fatty alcohols having a degree of ethoxylation of between 5 and 40 are particularly preferred. Examples of commercially obtainable surfactants are the Genapol types (Clariant AG). Silicone surfactants, in particular polyalkyl oxide-modified heptamethyltrisiloxanes, which are commercially obtainable e.g. as Silwet L-77®, and perfluorinated surfactants are likewise preferred. The concentration of the surface-active substances with respect to the total additive is in general between 1 and 30 wt. %. Examples of oil additives which comprise mixtures of oils or mineral oils or derivatives thereof with surfactants are Edenor ME SU®, Turbo Charge® (Syngenta Agro, CH) or Actipron® (BP Oil UK Limited, GB).

The surface-active substances mentioned can optionally also be used in the formulations by themselves, i.e. without oil additives.

The addition of an organic solvent to the oil additive/surfactant mixture may furthermore contribute towards an additional increase in the action. Suitable solvents are, for example, Solvesso® (ESSO) or Aromatic Solvent® (Exxon Corporation). The concentration of such solvents can be from 10 to 80 wt. % of the total weight. Such oil additives which are in the form of a mixture with solvents are described, for example, in U.S. Pat. No. 4,834,908. A commercially obtainable oil additive known from this is known by the name MERGE® (BASF Corporation). A further oil additive which is preferred according to the invention is SCORE® (Syngenta Crop Protection Canada).

In addition to the above mentioned oil additives, formulations of alkylpyrrolidones (e.g. Agrimax®) may furthermore also be added to the spray liquor to increase the action of the compositions according to the invention. Formulations of synthetic lattices, such as e.g. polyacrylamide, polyvinyl compounds or poly-1-p-menthene (e.g. Bond®, Courier® or Emerald®) can also be used for this. Solutions containing propionic acid, such as e.g. Eurogkem Pen-e-trate®, can furthermore also be admixed to the spray liquor as action-increasing agents.

The herbicidal formulations as a rule comprise 0.1 to 99 wt. %, in particular 0.1 to 95 wt. % of active compound mixture of the compound of the formula I with the compounds of the formula II, and 1 to 99.9 wt. % of a formulation auxiliary, which preferably comprises 0 to 25 wt. % of a surface-active substance. While concentrated compositions are conventionally preferred as commercial goods, the end user as a rule uses diluted compositions.

Various methods and techniques are suitable for using safeners of the formula II or compositions containing them for protecting crop plants from the harmful actions of herbicides of the formula I, such as, for example, the following:

i) Seed Dressing
a) Dressing of the seed with an active compound of the formula II formulated as a wettable powder by shaking in a vessel until uniform distribution over the seed surface is achieved (dry dressing). About 1 to 500 g of active compound of the formula S-I to S-X (4 g to 2 kg of wettable powder) per 100 kg of seed are used here.
b) Dressing of the seed with an emulsion concentrate of the active compound of the formula S-I to S-X by method a) (wet dressing).
c) Dressing by immersing the seed in a liquor with 100-1,000 ppm of active compound of the formula S-I to S-X for 1 to 72 hours and optionally subsequent drying of the seed (immersion dressing).

The dressing of the seed or the treatment of the sprouted seedling are of course the preferred methods of application, because the treatment with the active compound is directed entirely at the target crop. As a rules 1 to 1,000 g of antidote, preferably 5 to 250 g of antidote are used per 100 kg of seed, it being possible to deviate upwards or downwards from the limit concentrations stated (repeat dressing), depending on the method, which also allows the addition of other active compounds or micronutrients.

ii) Application as a Tank Mix
A liquid processed mixture of antidote and herbicide (reciprocal ratio of amounts of between 10:1 and 1:100) is used, the application rate of herbicide being 0.005 to 5.0 kg per hectare. Such tank mixes are applied before or after sowing, iii) Application into the Seed Furrow
The active compound of the formula II is introduced into the open sown seed furrow as an emulsion concentrate, wettable powder or as granules. After the seed furrow has been covered, the herbicide is applied by the pre-emergent method in the conventional manner.

iv) Controlled Release of the Active Compound
The active compound of the formula II is absorbed in solution on to mineral carrier granules or polymerized granules (urea/formaldehyde) and dried. A coating which allows the active compound to be released over a certain period of time can optionally be applied (coated granules).

In particular, preferred formulations have the following composition:
(%=percent by weight; active mixture of active compounds means the mixture of compound of the formula I with a compound of the formula S-I to S-X)

| Emulsifiable concentrates: | |
| --- | --- |
| Active mixture of active compounds: | 1 to 95%, preferably 60 to 90% |
| Surface-active agent: | 1 to 30%, preferably 5 to 20% |
| Liquid carrier: | 1 to 80%, preferably 1 to 35% |
| Dusts: | |
| Active mixture of active compounds: | 0.1 to 10%, preferably 0.1 to 5% |
| Solid carrier: | 99.9 to 90%, preferably 99.9 to 99% |
| Suspension concentrates: | |
| Active mixture of active compounds: | 5 to 75%, preferably 10 to 50% |
| Water: | 94 to 24%, preferably 88 to 30% |
| Surface-active agent: | 1 to 40%, preferably 2 to 30% |
| Wettable powders: | |
| Active mixture of active compounds: | 0.5 to 90%, preferably 1 to 80% |
| Surface-active agent: | 0.5 to 20%, preferably 1 to 15% |
| Solid carrier material: | 5 to 95%, preferably 15 to 90% |
| Granules: | |
| Active mixture of active compounds: | 0.1 to 30%, preferably 0.1 to 15% |
| Solid carrier: | 99.5 to 70%, preferably 97 to 85% |

The following examples explain the invention further, without limiting it.

Formulation Examples for Mixtures of Herbicides of the Formula I and Safeners of the Formula S-I to S-X) (%=Percent by Weight)

| F1. Emulsion concentrates | a) | b) | c) | d) |
| --- | --- | --- | --- | --- |
| Active compound mixture | 5% | 10% | 25% | 50% |
| Ca dodecylbenzenesulfonate | 6% | 8% | 6% | 8% |
| Castor oil polyglycol ether (36 mol EO) | 4% | — | 4% | 4% |
| Octylphenol polyglycol ether (7-8 mol EO) | — | 4% | — | 2% |
| NMP | — | — | 10% | 20% |
| Arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
| --- | --- | --- | --- | --- |
| Active compound mixture | 5% | 10% | 50% | 90% |
| 1-Methoxy-3-(3-methoxy-propoxy)-propane | — | 20% | 20% | — |
| Polyethylene glycol MW 400 | 20% | 10% | — | — |
| NMP | — | — | 30% | 10% |
| Arom. hydrocarbon mixture $C_9$-$C_{12}$ | 75% | 60% | — | — |

The solutions are suitable for use in the form of tiny drops.

| F3. Wettable powders | a) | b) | c) | d) |
| --- | --- | --- | --- | --- |
| Active compound mixture | 5% | 25% | 50% | 80% |
| Na ligninsulfonate | 4% | — | 3% | — |
| Na lauryl sulfate | 2% | 3% | — | 4% |
| Na diisobutyl-naphthalene-sulfonate | — | 6% | 5% | 6% |
| Octylphenol polyglycol ether (7-8 mol EO) | — | 1% | 2% | — |
| Highly disperse silica | 1% | 3% | 5% | 10% |
| Kaolin | 88% | 62% | 35% | — |

The active compound is mixed thoroughly with the additives and the mixture is ground thoroughly in a suitable mill. Wettable powders which can be diluted with water to give suspensions of any desired concentration are obtained.

| F4. Coated granules: | a) | b) | c) |
| --- | --- | --- | --- |
| Active compound mixture | 0.1% | 5% | 15% |
| Highly disperse silica | 0.9% | 2% | 2% |
| Inorg. carrier material (Average extension Æ 0.1-1 mm) such as e.g. $CaCO_3$ or $SiO_2$ | 99.0% | 93% | 83% |

The active compound is dissolved in methylene chloride, the solution is sprayed on to the carrier and the solvent is then evaporated off in vacuo.

| F5. Coated granules: | a) | b) | c) |
| --- | --- | --- | --- |
| Active compound mixture | 0.1% | 5% | 15% |
| Polyethylene glycol MW 200 | 1.0% | 2% | 3% |
| Highly disperse silica | 0.9% | 1% | 2% |
| Inorg. carrier material (Average extension Æ 0.1-1 mm) such as e.g. $CaCO_3$ or $SiO_2$ | 98.0% | 92% | 80% |

The finely ground active compound is applied uniformly, in a mixer, to the carrier material moistened with polyethylene glycol. Dust-free coated granules are obtained in this manner.

| F6. Extruded granules | a) | b) | c) | d) |
|---|---|---|---|---|
| Active compound mixture | 0.1% | 3% | 5% | 15% |
| Na ligninsulfonate | 1.5% | 2% | 3% | 4% |
| Carboxymethylcellulose | 1.4% | 2% | 2% | 2% |
| Kaolin | 97.0% | 93% | 90% | 79% |

The active compound is mixed with the additives and the mixture is ground and moistened with water. This mixture is extruded and then dried in a stream of air.

| F7. Dusts | a) | b) | c) |
|---|---|---|---|
| Active compound mixture | 0.1% | 1% | 5% |
| Talc | 39.9% | 49% | 35% |
| Kaolin | 60.0% | 50% | 60% |

Ready-to-use dusts are obtained by mixing the active compound with the carrier substances and grinding the mixture in a suitable mill.

| F8. Suspension concentrates | a) | b) | c) | d) |
|---|---|---|---|---|
| Active compound mixture | 3% | 10% | 25% | 50% |
| Ethylene glycol | 5% | 5% | 5% | 5% |
| Nonylphenol polyglycol ether (15 mol EO) | — | 1% | 2% | — |
| Na ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active compound is mixed intimately with the additives. A suspension concentrate from which suspensions of any desired concentration can be prepared by dilution with water is obtained in this way.

It is often more practical to formulate the active compound of the formula I and the mixing partner of the formula S-I to S-X individually and then to bring them together as a "tank mix" in water in the applicator in the desired mixing ratio shortly before application.

The ability of the safeners of the formula S-I to S-X to protect crop plants from the phytotoxic action of herbicides of the formula I is illustrated in the following examples.

BIOLOGICAL EXAMPLES

Example E1

Pre-Emergent Test on Maize

The test plants are sown in seed troughs under greenhouse conditions. A standard earth is used as the culture substrate. In a pre-emergent stage, the herbicides are applied both by themselves and in a mixture with safeners to the soil surface. The application is carried out with an aqueous suspension of the test substances, prepared from a 25% wettable powder (Example F3, b) or a suspension concentrate (Example F8), to achieve a field equivalent of 200 l/ha. The tests are evaluated after 14 days (100%=plants completely dead; 0%=no phytotoxic action on the plants).

TABLE E1

| Safener action on pre-emergent use on maize | | | |
|---|---|---|---|
| Comp. 1.41 WP 25% AW/W 1000 500 250 [g/ha] | Comp. 1.41 WP 25% AW/W 1000 500 250 [g/ha] Benoxacor WP 25% AW/W 50 25 12.5 [g/ha] | Comp. 1.41 WP 25% AW/W 1000 500 250 [g/ha] Dichlormid EC 250 GA/L 50 25 12.5 [g/ha] | Comp. 1.41 WP 25% AW/W 1000 500 250 [g/ha] Furilazole WP 5% AW/W 50 25 12.5 [g/ha] |
| 80 70 30 [%] | 60 40 20 [%] | 75 70 20 [%] | 20 10 0 [%] |

| Comp. 1.41 WP 25% AW/W 1000 500 250 [g/ha] | Comp. 1.41 WP 25% AW/W 1000 500 250 [g/ha] N-Isopropyl-4-(2-methoxy-benzoyl-sulfamoyl)-benzamide WP 25% AW/W 50 25 12.5 [g/ha] |
|---|---|
| 80 70 30 [%] | 25 25 20 [%] |

The test substances show good results. The same results are obtained when the compounds of the formula I are formulated according to the other above mentioned examples.

Example F1

Post-Emergent Test on Maize

The test plants are sown in containers under glasshouse conditions. A standard earth is used as the culture substrate. In a maize growth stage of one leaf (GS 11), the herbicides are applied both by themselves and in a mixture with safeners to the soil and leaf surface. The application is carried out with an aqueous suspension of the test substances, prepared from a 25% wettable powder (Example F3,b) or a suspension concentrate (Example F8), to achieve a field equivalent of 200 l/ha. The tests are evaluated after 28 days (100%=plants completely dead; 0%=no phytotoxic action on the plants).

TABLE F1

Safener action on post-emergent use on maize (Marista 11f)

|  | Comp. 1.27<br>WP 25% AW/W<br>150 75 37.5 [g/ha] |
| --- | --- |
| Comp. 1.27<br>WP 25% AW/W<br>150 75 37.5 [g/ha] | Benoxacor<br>WP 25% AW/W<br>37.5 19 9.5 [g/ha] |
| 40 10 0 [%] | 10 0 0 [%] |

Example G1

Pre-Emergent Test on Wheat and Barley

The test plants are sown in 48 well plates in a growth chamber. A sterilized standard earth is used as the culture substrate. In a pre-emergent stage, the herbicides are applied both by themselves and in a mixture with safeners to the soil surface. The application is carried out with an aqueous suspension of the test substances, prepared from a 25% wettable powder (Example F3,b), to achieve a field equivalent of 375 l/ha. The tests are evaluated after 14 days (100%=plants completely dead; 0%=no phytotoxic action on the plants).

TABLE G1

Safener action on pre-emergent use on wheat and barley

| Comp. 1.27<br>WP 25% AW/W<br>200 100 50 [g/ha] | Comp. 1.27<br>WP 25% AW/W<br>200 100 50 [g/ha]<br>Cloquintocet-mexyl<br>WP 25% AW/W<br>200 100 50 [g/ha] | Comp. 1.27<br>WP 25% AW/W<br>200 100 50 [g/ha]<br>MON4660<br>WP 25% AW/W<br>200 100 50 [g/ha] | Comp. 1.27<br>WP 25% AW/W<br>200 100 50 [g/ha]<br>Mefenpyr-diethyl<br>WP 25% AW/W<br>200 100 50 [g/ha] | Comp. 1.27<br>WP 25% AW/W<br>50 [g/ha] | Comp. 1.27<br>WP 25% AW/W<br>50 [g/ha]<br>Fenchlorazole-ethyl<br>WP 25% AW/W<br>50 [g/ha] |
| --- | --- | --- | --- | --- | --- |
| 50* 25* 40** [%] | 30* 15* 35** [%] | 15* 10* 35** [%] | 45* 12.5* 30** [%] | 40** [%] | 15** [%] |
| Comp. 1.57<br>WP 25% AW/W<br>100 50 [g/ha] | Comp. 1.57<br>WP 25% AW/W<br>100 50 [g/ha]<br>Cloquintocet-mexyl<br>WP 25% AW/W<br>100 50 [g/ha] | Comp. 1.57<br>WP 25% AW/W<br>100 50 [g/ha]<br>MON4660<br>WP 25% AW/W<br>100 50 [g/ha] | Comp. 1.57<br>WP 25% AW/W<br>100 50 [g/ha]<br>Mefenpyr-diethyl<br>WP 25% AW/W<br>100 50 [g/ha] | Comp. 1.57<br>WP 25% AW/W<br>50 [g/ha] | Comp. 1.57<br>WP 25% AW/W<br>50 [g/ha]<br>Fenchlorazole-ethyl<br>WP 25% AW/W<br>50 [g/ha] |
| 90* 70** [%] | 70* 25** [%] | 75* 50** [%] | 75* 50** [%] | 70** [%] | 40** [%] |

*test carried out on wheat (the value is the average value of two repetitions)
**test carried out on barley (the value is the average value of two repetitions)

The invention claimed is:

1. A herbicidal composition comprises a mixture of
a) a herbicidally active amount of a compound of the formula I

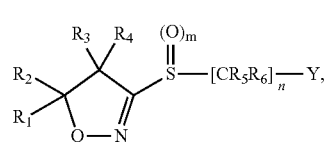

wherein
$R_1$ and $R_2$ are each independently of the other hydrogen or $C_1$-$C_{10}$alkyl
$R_3$ and $R_4$ are each independently of the other hydrogen, $C_1$-$C_{10}$alkyl or $C_1$-$C_{10}$haloalkyl;
m is an integer selected from 1 or 2;
$R_5$ and $R_6$ are each independently of the other hydrogen or methyl;
n is an integer selected from 1 or 2;
Y is phenyl or phenyl substituted by halogen, $C_1$-$C_6$alkyl or $C_1$-$C_6$haloalkyl, or
Y is diazole in which the diazole can be substituted by hydroxyl, halogen, $C_1$-$C_{10}$alkyl or $C_1$-$C_{10}$alkyl substituted by hydroxyl, $C_1$-$C_{10}$alkoxy, $C_1$-$C_4$haloalkyl, $C_1$-$C_4$haloalkoxy;
and
b) a herbicide-antagonistically active amount of a safener selected from the group consisting of cloquintocet-mexyl or a lithium, sodium, potassium, calcium, magnesium, aluminium, iron, ammonium, quaternary ammonium, sulfonium or phosphonium salt thereof, fenchlorazole-ethyl, mefenpyr-diethyl, isoxadifen-ethyl, furilazole or the R isomer thereof, benoxacor, dichlormid, MON4660, oxabetrinil, cyometrinil, the Z isomer thereof, fenclorim, N-cyclopropyl-4-(2-methoxy-benzoylsulfamoyl)-benzamide, N-isopropyl-4-(2-methoxy-benzoylsulfamoyl)-benzamide, naphthalic acid anhydride or flurazole, or a combination thereof.

2. The composition according to claim 1, comprises the compound of the formula I where
$R_1$ and $R_2$ are each independently of the other $C_1$-$C_{10}$alkyl.

3. The composition according to claim 2, comprises the compound of the formula I where
$R_3$ and $R_4$ are each independently of the other hydrogen or $C_1$-$C_{10}$alkyl.

4. The composition according to claim 3, comprises the compound of the formula I where
$R_5$ and $R_6$ are hydrogen.

5. The composition according to claim 4, comprises the compound of the formula I where
n is 1.

6. The composition according to claim 1, comprises the compound of the formula I where
Y is phenyl or phenyl substituted by halogen.

7. The composition according to claim 1, comprises the compound of the formula I where
Y is diazole or a diazole substituted by $C_1$-$C_{10}$alkyl, $C_1$-$C_4$haloalkyl, or $C_1$-$C_4$haloalkoxy.

8. The composition according to claim 1, where in the compound of the formula I Y is pyrazol-4-yl or pyrazol-5-yl.

9. The composition according to claim 1, wherein the compound of the formula I is 3-(5-difluoromethoxy-1-methyl-3-trifluoromethyl-1H-pyrazol-4-ylmethylsulfonyl)-5,5-dimethyl-4,5-dihydroisoxazole.

10. A method of combating weeds and weed grasses in crops of useful plants, wherein the useful plants, seed or cuttings thereof or a growing area thereof are treated simultaneously or at separate times with a herbicidally active amount of the herbicide of the formula I as defined in claim 1 and a herbicide-antagonistically active amount of the safener as defined in claim 1.

11. The method according to claim 10, wherein the crops of useful plants are maize.

12. The composition according to claim 9, wherein the safener is selected from the group consisting of cloquintocet-mexyl or a lithium, sodium, potassium, calcium, magnesium, aluminium, iron, ammonium, quaternary ammonium, sulfonium or phosphonium salt thereof, fenchlorazole-ethyl, mefenpyr-diethyl, benoxacor or MON4660.

* * * * *